United States Patent [19]

Parker et al.

[11] Patent Number: 5,247,075
[45] Date of Patent: Sep. 21, 1993

[54] TRI-AZA MACROCYCLES AND METAL COMPLEXES THEREOF

[75] Inventors: David Parker, Durham; Thomas A. Millican, Maidenhead, both of United Kingdom

[73] Assignee: Celltech Limited, Slough, United Kingdom

[21] Appl. No.: 784,601

[22] Filed: Oct. 22, 1991

Related U.S. Application Data

[63] Continuation of Ser. No. 363,683, Jun. 9, 1989, filed as PCT/GB88/00672, Aug. 12, 1988, abandoned.

[30] Foreign Application Priority Data

Aug. 12, 1987 [GB] United Kingdom ............. 8719041

[51] Int. Cl.$^5$ ............. K07D 255/02; C07D 403/02; C07D 403/14; A61K 31/55; A61K 31/555
[52] U.S. Cl. .................. 540/465; 540/474; 424/9; 424/1.1
[58] Field of Search .......... 540/474, 452; 514/183, 514/184

[56] References Cited

U.S. PATENT DOCUMENTS

| | | | |
|---|---|---|---|
| 4,174,319 | 11/1979 | Kobuke | 260/239 |
| 4,174,428 | 11/1979 | Tabushi et al. | 540/474 |
| 4,432,907 | 2/1984 | Wieder et al. | 436/500 |
| 4,472,509 | 9/1984 | Gansow et al. | 436/548 |
| 4,659,839 | 4/1987 | Nicolotti et al. | 548/546 |
| 4,671,958 | 7/1987 | Rodwell et al. | 514/2 |
| 4,678,667 | 7/1987 | Meares | 424/85 |

(List continued on next page.)

FOREIGN PATENT DOCUMENTS

| | | |
|---|---|---|
| 76267/87 | 2/1988 | Australia . |
| 0173629 | 8/1985 | European Pat. Off. . |
| 0188256 | 7/1986 | European Pat. Off. . |
| 0232751 | 8/1987 | European Pat. Off. ......... 540/474 |
| 88/08422 | 11/1988 | PCT Int'l Appl. . |
| 89/01476 | 2/1989 | PCT Int'l Appl. . |

OTHER PUBLICATIONS

Khaw et al., *Science*, 209, 295 (1980).
Krejcarek et al., *Biochem. Biophys. Res. Comm.*, 77, 581 (1977).

(List continued on next page.)

*Primary Examiner*—David B. Springer
*Attorney, Agent, or Firm*—Mathews, Woodbridge & Collins

[57] ABSTRACT

Tri-aza macrocycles of formula (I), wherein m and n, which may be the same or different, is each zero or an integer 1, 2, or 3; p is zero or an integer 1 or 2; q is zero or an integer from 1 to 6 inclusive; $R^1$, $R^2$ and $R^3$, which may be the same or different, is each a hydrogen atom or an alkyl, alkoxyalkyl, —$CO_2H$, —$SO_3H$, $PO_3H_2$ or aryl group; L is a covalent bond or linker group; Z is a hydrogen atom or a reactive functional group, with the proviso that when L is a covalent bond Z is a reactive functional group; and metal complexes and/or salts thereof are described together with processes for their preparation and compositions containing them. The compounds are useful for imaging and in the treatment of abnormal cell disorders, such as in the treatment of tumours, and are particularly suitable for coupling to other molecules such as proteins for use in diagnosis and therapy.

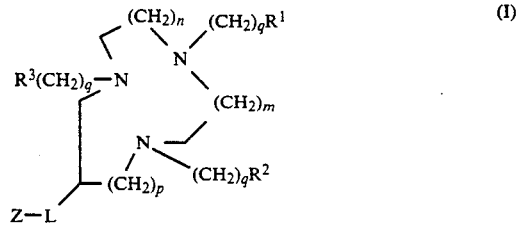

11 Claims, No Drawings

U.S. PATENT DOCUMENTS

| | | | |
|---|---|---|---|
| 4,877,600 | 10/1989 | Bonnemain et al. | 257/2 |
| 4,885,363 | 12/1989 | Tweedle et al. | 540/465 |
| 5,049,667 | 9/1991 | Schaefer et al. | 540/474 |
| 5,053,503 | 10/1991 | Dean et al. | 540/474 |

OTHER PUBLICATIONS

Childs, R. L. and Hnatowich, D. J., *J. Nuc. Med.* 26, 293 (1985).

Stetter, H., et al., *Angew. Chem. Int. Ed. Engl.*, 15, 686 (1976).

Loncin, J. F., et al., *Inorg. Chem.*, 25, 2646 (1986).

Moi, C. F., et al., *J. Am. Chem. Soc.*, 110, 6266 (1988).

Tweedle, M. F., et al., *J. Nuc. Med.*, 28, 705 (1988).

Goodwin, C. H., et al., *J. Nuc. Med.*, 27, 959 (1986).

Paik, C. H., et al., *J. Nuc. Med.*, 28, 572 (1987).

Paik, C. H., et al., *J. Nuc. Med.*, 29, 889 (1988).

Haseman, C. F., et al., *Eur. J. Nuc. Med.*, 12, 455 (1986).

Parker et al., *Pure & Appl. Chem.*, vol. 61, No. 9, 1637-1641 (1989).

Craig et al., *J. Chem. Soc. Chem. Commun.* (1989), pp. 794-796.

Cox et al., *J. Chem. Soc. Chem. Commun.* (1989), pp. 797-798.

Paik et al., *J. Nucl. Sci.*, vol. 30, No. 10, pp. 1693-1701 (Oct. 1989).

Paik et al., *Nucl. Med. Biol.*, vol. 16, No. 5, pp. 475-481 (1989).

Deshpande et al., *Nucl. Med. Biol.*, vol. 16, No. 6, pp. 587-597 (1989).

Deshpande et al., *The Journal of Nuclear Medicine.* "*Copper-67-Labeled Monoclonal Antibody Lym-1, A Potential Radiopharmaceutical for Cancer Therapy: Labeling and Biodistribution in RAJI Tumored Mice*", vol. 29, No. 2, pp. 217-225 (Feb. 1988).

Franz, J., et al., Abstract from Journal of Nuclear Medicine, Abstract No. 553, vol. 26, No. 5 (May 1985).

Franz et al., poster exhibited at 32nd Annual Meeting of the Society of Nuclear Medicine prior to May 1985.

Meares, Claude F., Protein Tailoring for Food and Medicine Uses edited by R. E. Feeny et al., "*Attaching Metal Ions to Antibodies*", pp. 339-352 (1986).

Goodwin, D. A., et al., Abstract of "*In Complex of a New Macrocyclic Bifunctional Chelator TETA*", presented at European Nuclear Medicine Congress Meeting at Barbican, London, Sept. 3-6 (1985).

Meares et al., Int. J. Cancer Suppl., 2, 99-102 (1988).

Meares et al., *Br. J. Cancer*, 62, 21-26 (1990).

Gransow et al., ACS Symposium Series, No. 241, "*Generator Produced Bi-212*" (1984).

Moi et al., *Anal. Biochem.*, 148, 249-253 (1985).

TRI-AZA MACROCYCLES AND METAL COMPLEXES THEREOF

This is a continuation of application Ser. No. 07/363,683, filed Jun. 9, 1989, filed as PCT/GB88/00672, Aug. 12, 1988, now abandoned.

FIELD OF THE INVENTION

This invention relates to functionalised tri-aza macrocycles, to metal complexes thereof, to conjugate compounds containing the functionalised tri-aza macrocycles and metal complexes thereof and to their use in diagnosis and therapy.

BACKGROUND OF THE INVENTION

The attachment of metal ions to proteins, peptides and other, smaller molecules is a fast expanding technology, which has numerous proven and potential applications in research, in industry and, particularly, in medicine.

In recent years, much of the impetus behind the development of this technology has been the ability to link metal ions to antibodies, especially monoclonal antibodies. Such metal labelled antibodies have found a widespread use, especially in medicine, where they have been employed, for example, to target the metal ion to a specific tissue type, both in vitro and in vivo. Thus, metal labelled antibodies have applications in locating specific tissue types (e.g. employing computer-aided tomographic techniques where the metal ion is in some way detectable) and in the treatment of cell disorders (e.g. treating mammalian tumours where the metal ion is a cytotoxic radionuclide).

Conventionally, attachment of the metal ion to a protein such as an antibody has been achieved by complexation by an acylic chelate such as a substituted diethylenetriaminepentaacetic acid [Gansow O. A. et al, Inorg. Chem., (1986), 25, 2772] or ethylenediaminetetraacetic acid [Meares, C. F. et al, Acc. Chem. Res., (1984), 17, 202] covalently linked to the antibody. Such acyclic complexes however tend to be unstable in vivo either as a result of acid-catalysed decomplexation or competitive chelate binding by $Ca^{2+}$ or $Zn^{2+}$ in serum, or as a result of competition from transferrin [Moerlein, S. M. et al, Int. J. Nuc. Med. Biol., (1981) 8, 277]. The lack of stability can result in uncomplexed metal atoms in the body which have a cytotoxic effect on healthy tissue (e.g. bone marrow) or which markedly reduce the signal-to-noise ratio of an imaging technique.

A possible alternative to the use of acyclic chelates in the labelling of antibodies is the use of macrocyclic ligands, which has been suggested in broad terms [Gansow O. A. et al. Am. Chem. Soc. Symp. Ser., (1984), 241, 215; UK Patent Specification Publication No. 2122641; and Moi M. K. et al, Anal. Biochem., (1985), 148, 249-253].

We have now found a new class of functionalised tri-aza macrocyles, members of which are able to form more kinetically inert complexes with metal ions than are chelating agents conventionally in use for the attachment of metal ions to proteins and other molecules. The macrocycles of the invention are particularly useful for attachment to proteins, especially antibodies, to provide conjugate compounds capable of binding metals to give complexes which are advantageously stable in vivo.

SUMMARY OF THE INVENTION

Thus, according to one aspect of the present invention we provide a compound of general formula (1):

[Structure of formula (1)]

wherein
m and n, which may be the same or different, is each zero or an integer 1, 2, or 3;
p is zero or an integer 1 or 2;
q is zero or an integer from 1 to 6 inclusive;
$R^1$, $R^2$ and $R^3$, which may be the same or different, is each a hydrogen atom or an alkyl, alkoxyalkyl, —$CO_2H$, —$SO_3H$, —$PO_3H_2$ or aryl group;
L is a covalent bond or a linker group;
Z is a hydrogen atom or a reactive functional group, with the proviso that when L is a covalent bond Z is a reactive functional group;
and metal complexes and/or salts thereof.

In the compounds of formula (1), alkyl groups represented by $R^1$, $R^2$ and $R^3$ may be for example $C_{1-6}$ alkyl groups such as methyl or ethyl groups. Alkoxyalkyl groups represented by $R^1$, $R^2$ or $R^3$ may be for example $C_{1-3}$alkoxy$C_{1-3}$alkyl groups e.g. methoxymethyl. When $R^1$, $R^2$ or $R^3$ is an aryl group it may be for example a substituted phenyl group, such as a group of formula

[Structure with $R^4$ and HO substituents on phenyl ring]

(where $R^4$ is a hydrogen atom or a $C_{1-6}$alkyl, e.g. methyl, $C_{1-3}$alkoxy$_{1-3}$alkyl, e.g. methoxymethyl, or $C_{6-12}$aryl, e.g. phenyl group).

In general, compounds of formula (1) in which $R^1$, $R^2$ and $R^3$ are the same are preferred. Compounds of this type in which q is an integer from 1 to 6 inclusive, particularly an integer 1, and $R^1$, $R^2$ and $R^3$ are —$SO_3H$, —$PO_3H$,

[Structure with $R^4$ and HO substituents on phenyl ring]

or, in particular, —$CO_2H$, are especially preferred.

In the compounds of formula (1), it will be appreciated that the nature of the group L when it is a linker group may be varied widely without substantially affecting the usefulness of compounds of formula (1) and the metal complexes thereof. Thus L may be any suitable organic radical and may be for example an optionally substituted aliphatic hydrocarbyl chain, optionally interrupted by one or more heteroatoms selected from —O— or —S— or by one or more —N(R⁵)— (where R⁵ is a hydrogen atom or a C₁₋₆alkyl group), —CON(R⁵)—, —N(R⁵)CO—, cycloaliphatic, aromatic, or heteroaromatic groups.

In the above definition, and in the same context whenever it appears below, the term "interrupted by" as applied to cycloaliphatic or aromatic groups is to be understood to also mean that these particular groups may additionally be present linked to the terminal carbon atom of the hydrocarbyl chain represented by L, at the opposite end of the chain to the carbon atom attached to the macrocycle.

Thus, for example, L may be an optionally substituted straight or branched C₁₋₂₀alkylene, C₂₋₂₀ alkenylene, or C₂₋₂₀ alkynylene chain, optionally interrupted by one or more —O— or —S— atoms or C₅₋₈cycloalkylene (e.g. cyclopentylene or cyclohexylene), C₆₋₁₂aromatic (e.g. phenylene or substituted phenylene), C₅₋₁₀heteroaromatic (e.g. furanyl, pyridyl), —N(R⁵)—, —CON(R⁵)— or —N(R)⁵CO— groups.

Examples of substituents which may be present on the chain L include halogen atoms, e.g. fluorine, chlorine, bromine, or iodine atoms or groups selected from C₁₋₆alkoxy (e.g. methoxy or ethoxy), hydroxy, nitro, —N(R⁶)(R⁷), [where R⁶ is a hydrogen atoms or a C₁₋₆alkyl group and R⁷ is a C₁₋₆alkyl group; e.g. —NHCH₃ or —N(CH₃)₂], or substituted amido, e.g. a group of formula —(CH₂)ₙCON(R⁸)(R⁹) [where n is zero or an integer 1 to 4 inclusive, R⁸ is a hydrogen atom or a C₁₋₆alkyl group, e.g. methyl and R⁹ is an optionally substituted C₁₋₆alkyl group].

Substituted alkyl groups represented by R⁹ include for example C₁₋₆alkyl groups substituted by one or more halogen atoms, or nitro, amino or hydroxy groups.

In general, in compounds of formula (1) the linker group is preferably an optionally substituted C₁₋₁₀alkylene, (especially C₁₋₆alkylene such as methylene, ethylene, propylene butylene, pentylene or hexylene) C₂₋₁₀ alkenylene or C₂₋₁₀ alkynylene chain optionally interrupted by one or more —O— or —S— atoms or cyclohexylene, phenylene, substituted phenylene, —NH—, —N(CH₃)—, —CONH—, —CON(CH₃)— —NHCO— or —N(CH₃)CO— groups.

Particular examples of linker groups represented by L include, for example, —(CH₂)_d— (where d is an integer 1 to 4 inclusive),

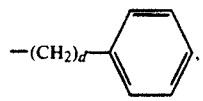,

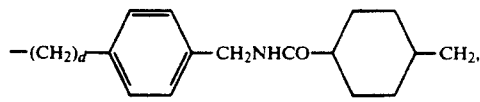

—(CH₂)_dNHCO(CH₂)_e— (where e is an integer 1 to 4 inclusive) and —(CH₂)_dNHCO(CH₂)_eOCH₂—.

The reactive functional group represented by Z in compounds of formula (1) may be any group capable of reacting with a thiol, amino, carboxyl, hydroxyl, aldehyde, aromatic or heteroaromatic group. Aromatic groups include, for example, phenolic groups. Heteroaromatic groups include for example imidazolyl groups.

Thus, Z may be, for example, a halogen atom, for example a chlorine, bromine or iodine atom, or a group selected from —SH, —NH₂, hydrazine (—NHNH₂) or a derivative thereof, [for example—N(CH₃)NH₂, —NHCONHNH₂, —NHCSNHNH₂, or phenyl hydrazine], —NCO, —NCS, —COR¹⁰, [where R¹⁰ is a halogen atom such as chlorine or bromine atom, or a N₃, C₁₋₆alkoxy, e.g. methoxy, C₆₋₁₂aryloxy (e.g. nitrophenyloxy or dinitrophenyloxy), imidyloxy (e.g. succinimidyloxy) or imidazolyoxy group], imide, e.g. maleimide, a vinyl group of formula —Het¹—C(-Het²)=CH₂ (where Het¹ and Het², which may be the same or different, is each a nitrogen containing heterocyclic group, e.g. a pyridyl group or Het¹ is a nitrogen containing heterocyclic group and Het² is a hydrogen atom), for example a vinyl pyridyl group of formula

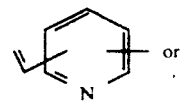 or

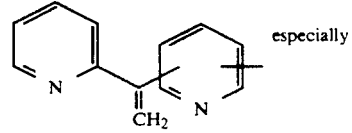 especially

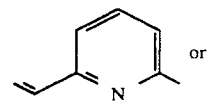 or

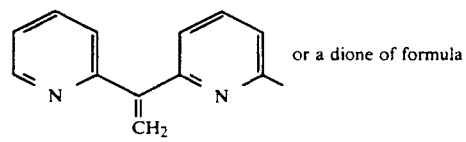 or a dione of formula

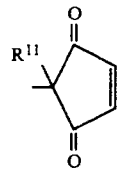

(where R¹¹ is a C₁₋₄alkyl e.g. methyl, group).

Metal complexes of the compounds of formula (1) include complexes wherein the metal is di- or tripositive and has a coordination number from 2 up to 6, especially 6. Examples of such metals include indium (In), gallium (Ga), cobalt (Co), copper (Cu), lead (Pb) and bismuth (Bi). In, Ga, Co and Cu are preferred, particularly In and Ga. In general the metal is preferably a radioactive isotope. Indium, especially ¹¹¹In, is particularly preferred.

In general, optimum binding of the metal to the compounds of formula (1) may be achieved by selection of the ring size and where appropriate by adjusting the potential coordination number by choice of the group —(CH₂)_qR¹, —(CH₂)_qR², and/or —(CH₂)_qR³ Thus a particularly important class of compounds of formula (1) is that wherein p is zero. Especially useful compounds are those wherein P is zero, m is an integer 1 and n is an integer 1. In general, compounds of formula (1) in which —(CH₂)_qR¹, —(CH₂)_qR² and —(CH₂)_qR³ is each —CH₂CO₂H are particularly useful.

Salts of the compounds of formula (1) include salts with bases, e.g. sodium or potassium salts, or acid addition salts such as hydrobromides or hydrochlorides. Pharmaceutically acceptable salts are particularly preferred.

A particularly useful group of compounds of the invention has the formula (1) wherein $R^1$, $R^2$, $R^3$, m, n, p and q are as defined for formula (1) and the groups —L and Z together represent a group (1) —$(CH_2)_r$—X—Y [where r is zero or an integer from 1 to 6 inclusive, X is a group —NH—,

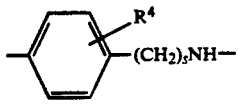

(where $R^4$ is a previously defined and s is zero or an integer 1 to 4 inclusive), —$(CH_2)_s$NHNH— or —$(OCH_2CH_2)_t$NH— (where t is an integer 1 to 6 inclusive) and Y is a group —$COZ^1$ or —$CO(R)Z^1$ (where R is a spacer group, and $Z^1$ is a group —$(CH_2)_r$Hal (where Hal is a halogen atom),

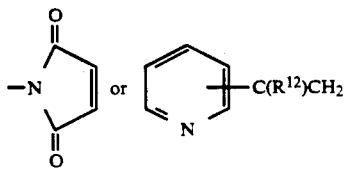

(where $R^{12}$ is a nitrogen containing aromatic heterocyclic group, for example a pyridyl group)], or (2) a group —$(CH_2)_r$NCS; and the metal complexes and/or salts thereof.

In compounds of this type, the spacer group R may be for example an alkylene, e.g. ethylene, alkoxyalkylene, e.g. methoxymethylene, aryl, e.g. phenylene, aralkylene, e.g. phenalkylene such as phenethylene, or cycloalkylalkylene, e.g. cyclohexylmethylene group.

A further particularly useful group of compounds according to the invention has the formula (1) wherein $R^1$, $R^2$, $R^3$, m, n, p and q are as defined for formula (1) and the groups L and Z together represent a group —$(CH_2)_r$XH (where r and X are as defined above) and the metal complexes and/or salts thereof.

An important group of compounds according to the invention has the formula (1a):

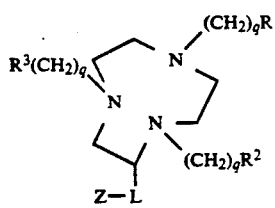

wherein $R^1$, $R^2$, $R^3$, L and Z are as defined for formula (1) and metal complexes and/or salts thereof.

Compounds of this type in which $R^1$, $R^2$ and $R^3$ is each —$CO_2H$ are particularly preferred.

Compounds of formula (1a) in which L is a linker group [particularly those specifically identified for compounds of formula (1)] are especially useful.

Z in compounds of formula (1a) is preferably a reactive functional group, [particularly those specifically identified for compounds of formula (1)], especially a group of formula —$Het^1$—$C(Het^2)$=$CH_2$ or a dione of formula

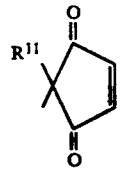

Indium complexes of the compounds of formula (1a) are particularly useful.

The compounds of formula (1) and the metal complexes and/or salts thereof have a diagnostic use as imaging agents in vitro and in vivo. The compounds of formula (1) and the metal complexes and/or salts thereof are also cytotoxic agents and may be used in the treatment of abnormal cell disorders, for example in the treatment of tumours.

For application of the compounds of formula (1) as imaging or cytotoxic agents, it is generally preferable to couple the compounds to other molecules such as proteins, especially antibodies, peptides or carbohydrates to form conjugate compounds, and the compounds of formula (1) are particularly well adapted for use in this respect.

Thus, according to a further aspect of the invention, we provide a conjugate compound which comprises a compound of formula (1), or a metal complex and/or salt thereof, coupled to a protein, peptide or carbohydrate.

The compound of formula (1) may be coupled through any thiol, amino, carboxyl, hydroxyl, aldehyde, aromatic or heteroaromatic group present in the protein, peptide or carbohydrate.

In a preferred aspect of the invention, we provide a conjugate compound which comprises a compound of formula (1) or a metal complex and/or salt thereof, coupled to an antibody.

It is to be understood that conjugate compound according to the invention may contain more than one molecule of a compound of formula (1) coupled to any one protein, peptide or carbohydrate molecule.

In a particular aspect, the invention provides conjugate compound of formula (2)

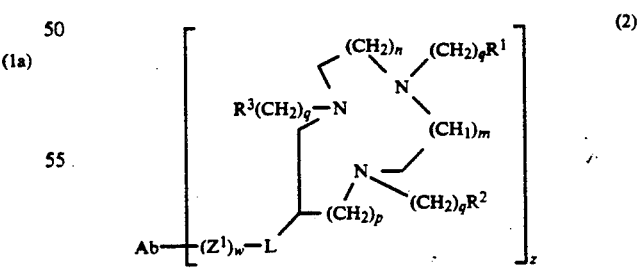

wherein
m, n, p, q, $R^1$, $R^2$, $R^3$, and L are as defined for formula (1);
$Z^1$ is the residue of a reactive functional group;
w is zero or an integer 1;
z is an integer 1 or more;
Ab is an antibody; and metal complexes and/or salts thereof.

In the compounds of formula (2), the residue of a reactive functional group represented by $Z^1$ may in general be the residue of a reactive functional group Z as defined for formula (1).

In particular, $Z^1$ may be for example —S—, —NH—, —NHN=, —N(CH$_3$)N=, —NHCONHN=, —NHCSNHN=, —N(Ph)N= (where Ph is phenyl, —NC(O)—, —NC(S)—, —CO—,

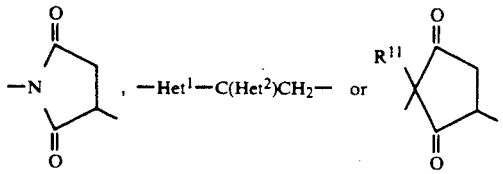

The antibody Ab in the conjugates of formula (2) may be a complete antibody molecule or a fragment thereof, or an analogue or either of these, provided that the antibody comprises of a specific binding region. Thus the antibody may be polyclonal, or, preferably, monoclonal, or a fragment thereof for example a Fab' or F(ab)$_2$' fragment. If desired the antibody may be a recombinant antibody, (i.e. an antibody which has been produced using recombinant DNA techniques). The antibody may be a chimaeric antibody comprising linked antibody fragments, each from a different source (see for example International Patent Specification No. WO 86/01533).

The antibody may be specific for any number of antigenic determinants, but is preferably specific for one antigenic determinant. Particular determinants include tumour cell-associated antigens, particularly mammalian tumour cell antigens for example oncofetal antigens such as carcinoembryonic antigen or alphafetoprotein.

A particular useful antibody is that known as B72.3 [Colcher, D. et al Proc. Nat. Acad. Sci. USA (1981), 78, 3199].

The antibody Ab will in general be coupled to the remainder of the conjugate of formula (2) (i.e. the macrocycle and linker) through any appropriate reactive atom or group, for example a nitrogen or, especially, sulphur atom, present in the antibody. It will be appreciated that any one antibody molecule may contain more than one reactive group capable of coupling with the macrocycle and linker. Thus, for example, z in the conjugates of formula (2) may be an integer 1, 2, 3, 4, 5, 6 or more depending on the number of macrocycles linked to any particular antibody molecule or fragment or analogue thereof.

Indium complexes of conjugates of formula (2) are particularly useful.

It is to be understood that the definitions and preferences expressed for m, n, p, q, $R^1$, $R^2$, $R^3$ and L in compounds of formula (1), and for classes of compounds of formula (1) are also applicable to conjugates of formula (2).

Particularly useful conjugate compounds according to the invention are those comprising a compound of formula (1a), or a metal complex and/or salt thereof, coupled to an antibody. The indium complexes of these conjugates are especially important.

The compounds of formulae (1) and (2) may be formulated for use in accordance with conventional practice, and thus according to a further aspect of the invention we provide a composition comprising a compound of formula (1) or a compound of formula (2) or a metal complex and/or salt thereof, together with one or more pharmaceutically acceptable carriers.

Particularly suitable compositions according to the invention are those adapted for parenteral administration, especially intravenous administration. Suitable formulations of this type include solutions of the compounds of formulae (1) or (2) in isotonic saline.

The quantities of compounds of formulae (1) or (2) used in formulations according to the invention will vary according to the intended use (i.e. imaging or therapy) and other variables such as the intended cell target, but may be easily determined in accordance with conventional practice for reagents of this type.

Compounds of the invention may be prepared by the following processes wherein the groups and symbols $R^1$, $R^2$, $R^3$, m, n, p, q, L, Z, Ab and z are as defined for formulae (1) and (2) except where stated otherwise. Where a metal complex is desired as a final product, the complexation with a metal atom may be carried out as a final step in the production process, as described below for the complexation of compounds of formulae (1), or alternatively it may be desirable to complex the metal at an earlier stage in the process, providing of course that the requisite macrocycle structure is present. In the following processes, it may be desirable to use starting materials in which the group Z is in a protected state, or which contain a precursor of the group, as discussed below.

Thus, according to a further aspect of the invention a compound of formula (1) or a metal complex thereof may be prepared by reaction of a corresponding compound of formula (3)

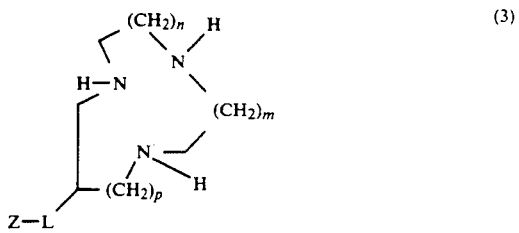

or a metal complex thereof, with a reagent $R^1(CH_2)_qD$ (where D is a displaceable group). Displaceable groups represented by D include for example halogen atoms, for example a bromine, chlorine or iodine atom.

The reaction may be performed in a solvent such as water or an organic solvent such as a nitrile e.g. acetonitrile or an alcohol e.g. isopropanol or an amide e.g. dimethylformamide in the presence of a base e.g. an inorganic base such as an alkali metal carbonate or hydroxide, e.g. sodium, potassium or caesium carbonate, or sodium, potassium or lithium hydroxide, at a high temperature e.g. the reflux temperature.

In this reaction, the group Z may need to be in a protected state. Conventional protecting groups may be used, depending on the nature of Z, and may be removed using standard procedures, once the desired reaction has been effected. Similarly, when the reagent $R^1(CH_2)_qD$ contains an acid group this may also need to be protected, for example as an ester e.g. a methyl ester. The acid may be re-generated after the desired reaction is complete, for example by hydrolysis using an acid such as sulphuric acid.

It will be appreciated that where it is desired to prepare a compound of formula (1) in which $R^1$, $R^2$ and $R^3$ are not the same this may be achieved by first selectively N-protecting the compound of formula (3) or a precursor using an appropriate amine protecting group(s), for example a p-toluenesulphonyl group as described below, in accordance with conventional practice. Reaction of the N-protected compound (3) with $R^1(CH_2)_qD$ followed by deprotection and further reaction as necessary with other reagents $R^1(CH_2(_qD$ then yields the desired compound in which $R^1$, $R^2$ and $R^3$ are not the same.

Where metal complexes of compounds of formulae (1) or (2) are required (or any other suitable macrocyclic intermediate described herein) these may be prepared by treating the compound with a metal salt (for example a metal halide) in an appropriate solvent for example an aqueous or non aqueous solvent, (e.g. acetonitrile, acetone, propylene carbonate, dimethylformamide or dimethylsulphoxide) at any suitable temperature from 0° C. to 100° C. such as 10° to 80° C. e.g. around 60° C.

In another process, a compound of formula (1) or a metal complex thereof wherein $R^1$, $R^2$ and $R^3$ is each $-(CH_2)_qPO_3H_2$ (where q is an integer 1 to 6) may be prepared by reaction of a compound of formula (3) or a metal complex thereof with phosphorous acid and an aldehyde $R^bCHO$ (where $R^b$ is a hydrogen atom or a $C_{1-5}$alkyl group) in the presence of an acid, such as hydrochloric acid at an elevated temperature, e.g. 100°-130° C.

Compounds of formula (1) may also be prepared by interconversion from other compounds of formula (1). Thus one functional group Z may be exchanged for another and, if desired a linker group L changed to another by appropriate manipulative reactions. For example, a compound of formula (1) where —L—Z is a group $-L^1-NHCO-L^2-Z$ (where $-L^1-NH-CO-L^2$ represents the group L) may be prepared by reaction of a corresponding compound wherein —L—Z represents $-L^1-NH_2$ with a reagent $R^bO-L^2-Z$ (where $R^b$ is for example an imide, such as succinimide, or a substituted phenyl group such as a p-nitrophenyl group) in the presence of a tertiary amine, such as diisopropylethylamine, in a solvent such as dimethylformamide.

Reagents of formula $R^bO-L^2-Z$ are either known compounds or may be obtained form known starting materials using methods analogous to those used for the preparation of the known compounds.

A conjugate compound of formula (2) or a metal complex thereof may be prepared by reaction of a corresponding compound of formula (1) or a metal complex thereof with an antibody Ab (as previously defined).

The reaction may be performed in a suitable solvent, for example an aqueous solvent such as a phosphate buffer, at an appropriate temperature, for example at 0°-30° C., especially 0°-10° C. e.g. 4° C.

The antibody Ab may be obtained using procedures well known in the art. If desired, before the coupling reaction, the antibody may first be treated to yield appropriate groups for reaction with the compound of formula (1). Thus for example the antibody may be subjected to oxidation, for example periodate oxidation to yield aldehyde groups, or, in particular, may be treated with a reagent [e.g. Traut's reagent (2-iminothiolane) using standard procedures to generate free sulphydryl groups in the molecule.

Salts of compounds of formulae (1) or (2) and their metal complexes may be prepared by conventional means, for example by reaction with an appropriate base or acid in a suitable aqueous solvent.

Intermediates of formula (3) in which p is an integer 1 may be prepared by reduction of a diamide of formula (4):

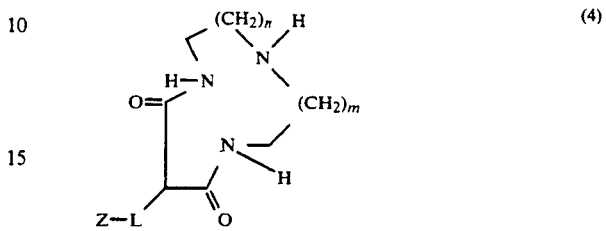

(where $R^{13}$ is a hydrogen atom or a nitrogen protecting group, for example a p-toluenesulphonyl group) using a reducing agent such as borane in a solvent such as tetrahydrofuran at a high temperature e.g. the reflux temperature, followed by treatment with an acid such as hydrochloric acid and, where necessary, followed by removal of the protecting group.

Intermediate diamides of formula (4) may be prepared by reaction of a diamine of formula (5):

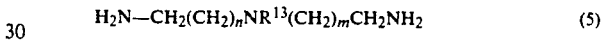

$$H_2N-CH_2(CH_2)_nNR^{13}(CH_2)_mCH_2NH_2 \quad (5)$$

with a diester of formula (6):

$$R^{14}O_2CCH(L-Z)CO_2R^{14} \quad (6)$$

(where $R^{14}$ is for example an alkyl group such as a methyl or ethyl group) in a solvent such as ethanol at reflux temperature, followed where appropriate by reaction with a reagent to introduce the protecting group $R^{13}$ (e.g. by reaction with p-toluenesulphonyl chloride in a solvent such as dichloromethane in the presence of a base such as triethylamine at e.g. reflux).

It will be appreciated that in the above reactions to obtain an intermediate of formula (3) the group Z may need to be in a protected form. Alternatively a precursor of the group may be used. For example where Z is an amino group, the amino function may be generated from a corresponding nitrile during the reduction of a diamide of formula (6). The starting material for this reaction may be prepared from a compound of formula (6), in which Z is a nitrile group, as described previously.

The intermediate compounds of formula (3) and (4) are novel and form further aspects of the invention.

Intermediates of formula (3) in which p is zero or an integer 2 may be prepared by deprotection of a compound of formula (7)

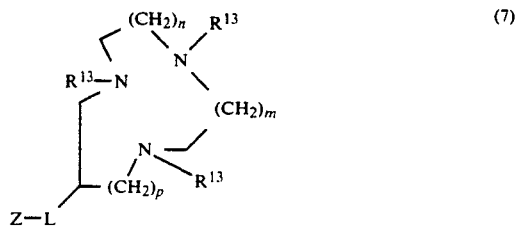

(where p is as just defined, R¹³ is a protecting group as defined above and —L—Z is as defined previously). The deprotection will depend on the nature of the protecting group R¹³. Thus, for example, when R¹³ is a p-toluenesulphonyl group removal of this may be achieved by treatment of the compound of formula (7) with an acid, for example HBr-acetic acid, in the presence of phenol at a high temperature, or by reaction with lithium in liquid ammonia in the presence of an alcohol such as ethanol.

Intermediates of formula (7) may be prepared by treating a compound of formula (8)

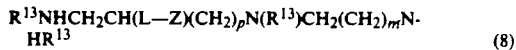  (8)

with a compound R¹³OCH₂(CH₂)ₙOR¹³ in the presence of a base such as caesium carbonate in a solvent such as dimethylformamide.

Intermediates of formula (8) may be prepared by reduction of compounds of formula (9)

$H_2NCOCH(L-Z)(CH_2)_pNHCO(CH_2)_mNHR^{13}$ (9)

using for example borane as described above with intermediates of formula (4), following by protection using a suitable protecting agent, for example p-toluenesulphonyl chloride as described previously.

Intermediate of formula (9) may be prepared by reacting an appropriate substituted amino acid of formula (10)

$R^{11}O_2CCH(L-Z)(CH_2)_pNH_2$ (10)

(where R¹¹ is a previously defined) with a reagent HA-lOC(CH₂)ₘNHR¹³ (where Hal is a halogen atom) in the presence of a base such as triethylamine, followed by reaction with ammonia in a solvent such as methanol.

The intermediates of formula (10) are either known compounds or may be prepared by methods analogous to those used for the preparation of the known compounds.

In an alternative process, intermediates of formula (7) in which p is zero may be prepared by reaction of a compound of formula (11)

$R^{13}NHCH(L-Z)CH_2N(R^{13})CH_2(CH_2)_mNHR^{13}$ (11)

with a compound R¹³(OCH₂(CH₂)ₙOR¹³ in the presence of a base such as caesium carbonate in a solvent such as dimethylformamide.

Intermediates of formula (11) may be prepared by reduction of compounds of formula (12)

$H_2NCH(L-Z)CONHCH_2(CH_2)_mNHR^{13}$ (12)

using for example borane as described above, followed by reaction to introduce the protecting group R¹³, for example with p-toluenesulphonyl chloride as described previously.

Intermediates of formula (12) may be prepared by reaction of an appropriately substituted amino acid of formula (13)

$H_2NCH(L-Z)CO_2R^{14}$ (13)

(where R¹⁴ is as defined above with a diamine H₂NCH₂(CH₂)ₘNH₂ at a high temperature, e.g. the reflux temperature.

Amino acids of formula (13) are either known compounds or may be prepared by methods analogous to those used for the preparation of the known compounds.

The invention is illustrated by the following Examples.

DESCRIPTION OF SPECIFIC EMBODIMENTS

Intermediate 1

3-para-Cyanobenzyl-1,5,9-triaza-2,4-dioxocyclododecane

To a solution of p-cyanobenzyldiethyl malonate (5.50 g) in dry ethanol (500 ml) was added 1,7-diamino-4-azaheptane (2.62 g) and the mixture was refluxed for 5 days. After evaporation of solvent, the residue was chromatographed on silica [eluting with 1% NH₄OH, 40% methanol, 59%. CH₂Cl₂] to yield the title compound as a colourless solid (990 mg) m.p. 263°-265° C. m/e (chemical ionisation, NH₃) 315 (M⁺+1), 316 (M⁺+2); ∂_H (CDCl₃) 7.53 (2H, d), 7.50 (2H, br NHCO), 7.34 (2H, d), 3.65 (2H, mult.) 3.34 (2H, d), 3.23 (1H, mult.), 3.21 (2H, d), 2.9–2.8 (2H, mult.), 2.68 (2H, mult.) 1.73 (2H, mult.), 1.56 (2H+1H, mult.).

Intermediate 2

3-para-Cyanobenzyl-1,5,9-triaza-5-p-toluenesulphonyl-2,4-dioxocyclododecane

To a suspension of Intermediate 1 (628 mg) in dichloromethane (20 ml), was added triethylamine (200 mg) and p-toluenesulphonyl chloride (381 mg) and the mixture was heated at reflux for 18h. After filtration, the residue was chromatographed on silica (CH₂Cl₂-methanol) to yield the title compound as a colourless foam (749 mg) m/e [desorption chemical ionisation (NH₃)] 469 (M⁺+1), 468, 289, 255, 215, 157, i.e. (KBr), 3300 (NH), 2215 (CN), 1670, 1640, 1530 (br.s.), 1160 cm⁻¹ ∂_H(CD₃OD), 7.74 (2H,d), 7.65 (2H,d), 7.43 (4H, mult.), 3.49–3.11 (9H,m.), 2.91–2.82 (2H,m), 2.47 (3H,s), 1.74 (2H,m), 1.60 (2H,m).

Intermediate 3

3-para-Aminomethylbenzyl-1,5,9-triaza-5-tosyl-cyclododecane

To a suspension of Intermediate 2 (468 mg) was added 1M borane-tetrahydrofuran solution (20 ml) and the mixture was refluxed for 36h. Excess borane was destroyed by slow addition of methanol (5 ml) and solvents were removed under reduced pressure to yield a residue which was treated with 6M HCl (15 ml) and refluxed for 3h. After removal of water, the residue was taken up in the minimum volume of 2M KOH solution and extracted with chloroform (3×20 ml). Removal of solvent geve the title compound as a colourless oil (400 mg). m/e (chemical ionisation, NH₃) 446 (M⁺+2), 445 (M⁺+1), 324, 289, 229. ∂_H(CDCl₃) 7.67 (2H,d), 7.29 (2H,d), 7.23 (2H,d), 7.11 (2H,d), 3.83 (2H,s), 3.27–3.16 (4H,m), 2.86–2.77 (4H,m), 2.62–2.52 (4H,m), 2.48–2.45 (2H,d), 2.42 (3H,s), 2.17–1.91 (4H,m), 1.78∝1.68 (4H,m). ∂_C (CDCl₃), 143.2, 129.6, 129.9, 127.4, 127.1, 51.8, 46.1, 45.9, 45.2, 38.3, 37.7, 26.6, 21.5, i.e. (Nujol) 3300 (NH), 1590, 1160 cm⁻¹.

Intermediate 4

3-para-Aminomethylbenzyl-1,5,9,-triazacyclododecane tetrahydrobromide

To a solution of Intermediate 3 (400 mg), in HBr-acetic acid (45%, 25 ml) was added phenol (0.5 g) and the mixture was heated at 110° C. for 36h. After cooling a colourless solid was filtered, washed with acetone and dried ($K_2CO_3$) to yield the title compound, 525 mg) i.r. (KBr) 3600-3300 (br,NH), 2890, 1585 cm$^{-1}$ $\partial_H$ ($D_2O$) 7.11 (2H, d), 7.06 (2H,d), 3.79 (2H,s), 3.13-2.78 (12H,m), 2.56 (2H,d), 2.29 (1H,m), 1.81-1.69 (4H,m).

Intermediate 5

3-para-Acetamidomethylbenzyl-1,5,9-triazacyclododecane

To an aqueous solution of Intermediate 4 (525 mg pH6.8, 5 ml) was added a solution of p-nitrophenylacetate (543 mg) in dioxan (5 ml) and the mixture was stirred at 35° C. for 18h. After washing with ether (3×10 ml) the pH of the solution was raised to 13.5, and the solution extracted with chloroform (5×10 ml), dried ($K_2CO_3$), filtered and evaporated to give the title compound as a colourless oil (228 mg), m/e (chemical ionisation, $NH_3$) 334 ($M^+ +2$), 333 ($M^+ +1$). $\partial_H$ ($CDCl_3$) 7.25 (2H,d), 7.16 (2H,d) 4.39 (2H,d), 3.48 (2H,s), 2.87-2.53 (14H,m), 2.17 (1H,m), 2.02 (3H,s) 1.85-1.40 (7H,m).

Intermediate 6

3-para-Acetamidomethylbenzyl-N,N',N''-tricarboethoxymethyl-1,5,9-triazacyclododecane To a solution of Intermediate 5 (166 mg) in dry acetonitrile (5 ml) was added anhydrous sodium carbonate (170 mg) and ethyl bromoacetate (251 mg) and the mixture refluxed for 18h. After filtration and removal of solvent, the residue was chromatographed on neutral alumina (activity II/III, 3% methanol/$CH_2Cl_2$) to yield the title compound as a colourless gum (59 mg) m/e (chemical ionisation, $NH_3$) found 590.372253 (calculated 590.3679504) 591 ($M^+ +1$), 590 ($M^+$) 547, 503, 428, i.r. (liquid film) 3280 (NHCO), 2920, 1735, 1660 cm$^{-1}$. $\partial_H$($CDCl_3$) 7.16 (4H,m), 5.80 (1H,m), 4.39 (2H,d), 4.13 (6H,q), 3.23 (4H,s), 3.19 (2H,s), 2.85-2.53 (8H,m), 2.45-2.23 (7H,m), 2.02 (3H,s). 1.78-1.60 (4H,m), 1.29-1.23 (6H, +3H,t+t).

Intermediate 7

2,6-Diamino-1-hexanoic acid, ethylenediamine ester 2,6-Diamino-1-hexanoic acid, methyl ester, dihydrochloride (10.283 g) was added (as solid) in small batches over a 50 minute period to ethylenediamine (100 ml) at 90° C., with stirring. The temperature of the reaction mixture was then raised to 140° C. for 6 hrs, after which the ethylenediamine was removed by vacuum distillation to yield a brown residual oil which was taken up in 4M NaOH (25 ml) and dried in vacuo. Methanol (30 ml) was added, the solution was filtered, the methanol removed (Buchi) and the residue dissolved in $CH_2Cl_2$ (100 ml), then filtered, and the filtrate rotovated down to give the title compound as a clear brown oil (8.827 g). i.r (thin film) 3300/3280 3060 2930 1650 1570 1470 1320 cm$^{-1}$.

Intermediate 8

1,5,9-Triamino-3-aza-nonane, tetrahydrochloride

Intermediate 7 (3.754 g) and borane-tetrahydrofuran (130 mmol, 130 ml) was refluxed for 21 hours. After removal of volatiles, the aminoborane was washed with methanol (2×100 ml) and hydrolysed with 6M HCl (150 ml. 110° C.) for 3 hours. The resulting solution was evaporated, methanol (20 ml) added and further evaporated to yield the title compound (6.279 g) as a white hygroscopic solid.

Intermediate 9

1,5-Diamino-(9-N-benzamidyl)1-3-aza-nonane

Intermediate 8 (6.16 g) and potassium hydroxide (4.4 g) was dissolved in water (50 ml) and, with stirring, copper carbonate (2.603 g) was added. Continued stirring over 30 minutes at 50° C. yielded an intense blue solution which was cooled to 0° C. and benzoyl chloride 2.5 ml added in 0.25 ml portions over 90 minutes keeping the pH greater than 9 with periodic addition of KOH pellets. The solution was then allowed to stir at room temperature for 1 hour, then filtered and the filtrate treated with $H_2S$ over 30 minutes. The solution was filtered once again to give a greeny-yellow filtrate which on addition of KOH to pH14 went a dark green, with a small amount of green precipitate. This was filtered off, the filtrate reduced in volume to 40 ml of exhaustively extracted (13x) with $CH_2Cl_2$, dried ($K_2CO_3$), and evaporated to yield the title compound as a pale yellow oil (2.152 g). $^1$H-NMR (250 MHz), $\delta$($CDCl_3$): 1.57 (m, 16H, $CH_2$, NH, $NH_2$) 2.37 (dd, 1H, CH), 2.67 (m 3H, $CH_2N$), 2.79 (m, 3H, $CH_2N$).

Intermediate 10

1,5-Ditosylamino-3-tosyl-(9-N-benzamidyl)-3-aza-nonane

Intermediate 9 (1.978 g) in dry $CH_2Cl_2$ (50 ml) was added dropwise to a solution of tosyl chloride (5.087 g), in dry $CH_2Cl_2$ (50 ml) and the mixture was then allowed to stir for 2½ hours at room temperature. The solution was then washed with water (20 ml) dried ($K_2CO_3$), filtered and evaporated to an oily brown residue which was redissolved in $CH_2Cl_2$ (10 ml). After a few minutes a white solid precipitated which was collected by filtration and washed with $CH_2Cl_2$ to give the title compound (1.701 g).

TLC (silica; 5% methanol in $CH_2Cl_2$) Rf 0.44 m/e [desorption chemical ionisation (methanol)] 741 ($M^+ +1$), 740 ($M^+$).

Intermediate 11

2-(4-N-Benzamidyl)butyl-N',N'''-tritosyl-1,4,7-triazacyclononane

Intermediate 10 (3.70 g) was dissolved in anhydrous dimethylformamide (200 ml) and caesium carbonate (3.26 g) added under dry nitrogen. A solution of ethylene glycol ditosylate (1.85 g), in anhydrous dimethylformamide (50 ml) was slowly added, with stirring, over 4 hours. Stirring was continued overnight (20° C.) and the temperature then raised to 65° C. for 3 hours. The dimethylformamide was removed under reduced pressure and the residue dissolved in chloroform (200 ml), washed with water (3×30 ml) and dried ($K_2CO_3$). The residue was dissolved in the minimum volume of $CH_2Cl_2$ (15 ml) and ethanol added slowly until turbidity. The flask was chilled to −20° C. overnight and the title compound (2.6 g) separated as a colourless solid. m/e [desorption chemical ionisation (CHCl₃)]: 767(M⁺+1), 766 (M⁺) (100%).

Intermediate 12

2-(4-N-Benzamidyl)butyl-1,4,7-triazacyclononane

To Intermediate 11 (1.2 g) in a flask under nitrogen was added ethanol (2 ml), and liquid ammonia (100 ml) then allowed to condense in the flask. Lithium metal (0.38 g) was added and an intense blue colour developed which discharged within 20 minutes. After evaporation of NH₃ (4 hours) water (20 ml) was added and the solution evaporated to dryness, taken up to 6 MHCl (20 ml) washed with ether (3×20 ml), evaporated to dryness and redissolved in 6M KOH (20 ml) and extracted with dichloromethane (5×20 ml). The extract was dried and evaporated to yield the title compound (360 mg). m/e [desorption chemical ionisation (methanol)]: 305 (M⁺+1)

EXAMPLE 1

3-para-Aminomethylbenzyl-1,5,9-triazacyclododecane-N,N',N''-triacetic acid

Intermediate 6 (59 mg) was added to 6M HCl (5 ml), and refluxed at 110° C. for 18 hours, to yield the title compound following romoval of volatiles. The title compound was homogeneous by cation-exchange hplc, (Synchropak TSK DEAE, ammonium acetae (pH7), CH₃CN). m/e (FAB, glycerol) 465 (M⁺+1), 464 (M⁺).

EXAMPLE 2

(a) The compound of Example 1 (2.6 mg) in 0.5M 1,4-piperazine bis(ethanesulphonic acid) [PIPES; pH6.8, 300μ] was added to the sulphite salt of the n-hydroxysuccinimide ester of N-(4-carboxycyclohexyl-methyl)maleimide [Yamada et al, Eur. J. Biochem., (1979). 101, 395; 10 mg] in 1,4-dioxan (300 ml). The reaction was monitored by high performance liquid chromatography (hplc) using a polymer reverse phase column (PLRP, 100 Å, 15 cm×4.4 mm internal diameter) using the following conditions:

| TIME | % A | % B | % C |
|------|-----|-----|-----|
| 0 | 87 | 10 | 3 |
| 20 | 40 | 10 | 50 |
| 20.1 | 87 | 10 | 3 |

A=H₂O, B=1M ammonium acetate pH 6.5, C=CH₃CN. λ=268 nm, Flow rate=1.0 ml/min.

The desired product eluted at 19 minutes and was purified preparatively to give a solution (approximately 5 ml, 500 μM) of a compound of formula (1) wherein m is 2, n is 2, p is 1, —(CH₂($_q$R¹, —(CH₂)$_q$R² and —(CH₂)$_q$R³ is each —CH₂CO₂H, and —L—Z is a group

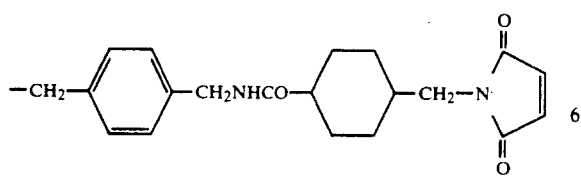

(b) The solution prepared in 2(a) was adjusted to pH5 using acetic acid/water (25% v/v) and to 90 μl of this was added ¹¹¹InCl₃(10 μl, 112 μCi) and the reaction left at 55° C. for 1 hour. The mixture was then purified by hplc using the above programme and radiometric detection. The ¹¹¹In complex of the compound of formula (1) described above eluted at 18 minutes and was collected and concentrated to a low volume (approximately 100 μl).

(c) B72.3 monoclonal antibody [Colcher, D. et al Proc. Nat. Acad. Sci. USA (1981), 78, 3199; 1.2 mg, previously modified with Traut's reagent to liberate 5.7 thiols/antibody] in 0.3M phosphate buffer (containing 2 mM ethylenediaminetetraacetic acid; pH8.0; 110 μl) was added to the ¹¹¹In complex prepared in 2(b) and the mixture was incubated at 4° C. overnight then purified by PD-10 gel filtration chromatography to yield the ¹¹¹In complex of the conjugate of formula (2) wherein m is 2;, n is 2, p is 1, —(CH₂)$_q$R² and —(CH₂)$_q$R³ is each —CH₂CO₂H, L—Z¹ is

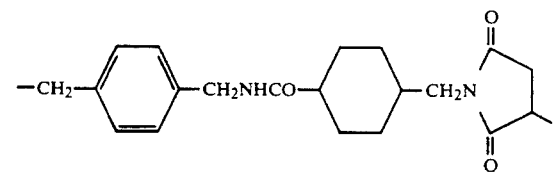

z is an integer 1 or more and Ab is a B72.3 monoclonal antibody.

The conjugate was injcted in mice and the tissue distribution of the ¹¹¹In determined after 4 hours and 24 hours. The results are as shown in Table 1.

TABLE 1

| | Tissue | | | |
|---|---|---|---|---|
| | 4 Hours* | | 24 Hours** | |
| | % Dose/g Tissue | % Total Injected Dose | % Dose/g Tissue | % Total Injected Dose |
| Blood | 32.4 | 60.9 | 21.275 | 47.52 |
| Kidneys | 12.32 | 2.88 | 8.92 | 2.495 |
| Liver | 8.605 | 12.36 | 6.555 | 9.955 |
| Lungs | 15.16 | 2.215 | 9.315 | 1.45 |
| Spleen | 6.075 | 0.41 | 6.44 | 0.53 |
| Stomach | — | 0.7 | — | 0.645 |
| Small Intestine | — | 2.39 | — | 2.6 |
| Large Intestine | — | 2.935 | — | 2.175 |

*Mean of 2 mice
**Mean of 2 mice

In control experiments using free ¹¹¹In and ¹¹¹In bound to macrocyle only, all radioactivity was cleared from the tissues in a few hours. The persistance of ¹¹¹In the tissues after 24 hours as shown in Table 1 illustrates that the indium complex described in 2(c) has been bound by the antibody.

EXAMPLE 3

2-O-(6-ethenyl)-2-(pyridyl)methyl-N-[4-(2-perhydro-1,4,7-triazaninine-1,4,7-tri(2-acetic acid)butyl)ethanamide].

(a)

2-(4-N-Benzamidyl)butylperhydro-1,4,7-triazanonine-1,4,7-tri(2-acetic acid)

Lithium hydroxide monohydrate (14.5 mg) and 2-bromoacetic acid (31.0 mg) were added to Intermediate 12 (20 mg) in water (0.476 ml), the pH being kept at pH12 and above using additional lithium hydroxide as necessary. The solution was heated to 80° C. and the reaction monitored by reverse phase high performance liquid chromatography using Lys1 and the following programme:

| BUFFERS: | A = 0.1% trifluoroacetic acid/H₂O | |
|---|---|---|
| | B = 0.1% trifluoroacetic acid/CH₃CN | |
| λ = 254 nm; flow = 1.4 ml/minute | | |
| Time (T; min) | % A | % B |
| 0 | 95 | 5 |
| 20 | 5 | 95 |
| 25 | 5 | 95 |

Equilibration time = 10 minutes.

During the reaction a major peak built up within 30 minutes at T=11.43 with a minor peak at T=12.077. The major peak was assumed to be the dicarboxylated species and further additions of acid were therefore made to the reaction solution over a 24 hour period to maximise the yield of the product at T=12.077.

After 24 hours the reaction solution was subjected to preparative high performance liquid chromatography using Lys 1 to yield the title compound (100.9 mg) of Part (a). m/e 479 (M+ +1).

(b)
2-(4-Amino)butylperhydro-1,4,7-triazanonine-1,4,7-tri(2-acetic acid)

The compound of Part (a) [5 mg] was dissolved in 6M HCl (3 ml) and heated at 130° C. under nitrogen for 18 hours. The solution was dried in vacuo and the residue redissolved in dry dimethylformamide. The drying and redissolving in dimethylformamide was repeated three times to yield the title compound of Part (b) which was used in the following reaction without further purification.

2-O-(6-ethenyl)-2-(pyridyl)methyl-N-[4-(2-perhydro-1,4,7-triazanonine-1,4,7-tri(2-acetic acid)butyl)ethanamide]

(c) The p-nitrophenyl ester of 2-vinyl, 6-methoxyacetic acid pyridine (3.0 mg) in dry dimethylformamide (0.5 l) was added to the amine prepared in Part (b) above, followed by diisopropylethylamine (9.0 mg). The reaction was monitored by reverse phase high performance liquid chromatography using Lys1 and the programme described in Part(a) above. The product which was observed at T=10.5 min was collected and lyophillised to give the title compound [3.0 mg] m/e (FAB, glycerol) 550 (M+ +1). The title compound elutes at T=8.10 on anion exchange chromatography (Synchropak AX101) using the following programme:

We claim:
1. A member selected from the group consisting of
(i) a coupling compound of the formula:

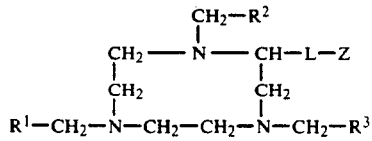

wherein
each of $R^1$, $R^2$, and $R^3$ is —COOH, —SO₃H, or —PO₃H₂;

Z is selected from the group consisting of halo, thiol, amino, hydrazino, —N=C=O, —N=C=S, —COR¹⁰, imido, vinylpyridinyl, [1-(pyridyl)eth-1-en-1-yl]pyridinyl, and 2-R¹¹-cyclopent-4-ene-1,3-dione, in which $R^{10}$ is halo, azido, alkoxy of 1 to 6 carbon atoms, aryloxy of 6 to 12 carbon atoms, imidyloxy, or imidazolyloxy and $R^{11}$ is alkyl of 1 to 4 carbon atoms; and L is an optionally substituted hydrocarbyl chain which optionally includes one or more members selected from the group consisting of —O—, —S—, —N(R⁵)—, —CON(R⁵)—, —N(R⁵)CO—, a cycloaliphatic ring, an aromatic ring, and a pyridine ring, in which $R^5$ is hydrogen or alkyl of 1 to 6 carbon atoms;

(ii) a complex of said compound with a di or tripositive metal having a co-ordination number of from 2 to 6; and (iii) a pharmaceutically acceptable salt of said compound.

2. A member selected from the group consisting of
(i) a coupling compound of the formula:

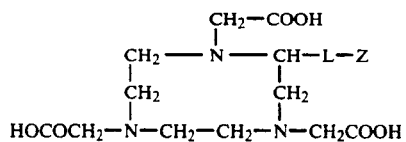

wherein
Z is selected from the group consisting of halo, thiol, amino, hydrazino, —N=C=O, —N=C=S, —COR¹⁰, imido, vinylpyridinyl, [1-(pyridyl)eth-1-en-1-yl]ppyridinyl, and 2-R¹¹-cyclopent-4-ene-1,3-dione, in which $R^{10}$ is halo, azido, alkoxy of 1 to 6 carbon atoms, aryloxy of 6 to 12 carbon atoms, imidyloxy, or imidazolyloxy and $R^{11}$ is alkyl of 1 to 4 carbon atoms; and L is an optionally substituted hydrocarbyl chain which optionally includes one or more members selected from the group consisting of —O—, —S—, —N(R⁵)—, —CON(R⁵)—, —N(R⁵)CO—, a cycloaliphatic ring, an aromatic ring, and a pyridine ring, in which $R^5$ is hydrogen or alkyl of 1 to 6 carbon atoms;

(ii) a complex of said compound with a di or tripositive metal having a co-ordination number of from 2 to 6; and (iii) a pharmaceutically acceptable salt of said compound.

3. A metal complex according to claim 2 wherein the metal is gallium.

4. A coupling compound according to claim 2 wherein L is —(CH₂)_d—, —(CH₂)_d-(phenylene)—, —(CH₂)_d-(phenylene)-CH₂NHCO-(cyclohexanediyl)—, —(CH₂)_d—NHCO—(CH₂)_e—, or —(CH₂)_d—NHCO—(CH₂)_eOCH₂—.

5. A coupling compound according to claim 2 wherein Z is amino, 6-vinylpyridin-1-yl, 6-[1-(1-pyridyl)eth-1-en-1-yl]pyridin-1-yl, or 2-R¹¹-cyclopent-4-ene-1,3-dione.

6. A metal complex according to claim 2 wherein the metal is indium, gallium, cobalt, copper, lead, or bismuth.

7. A metal complex according to claim 2 wherein the metal is indium.

8. The coupling compound according to claim 2 wherein —L—Z is:

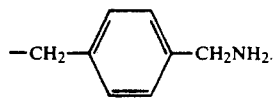

9. The coupling compound according to claim 2 wherein —L—Z is:

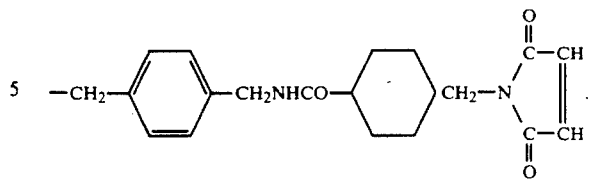

10. The coupling compound according to claim 2 wherein —L—Z is:

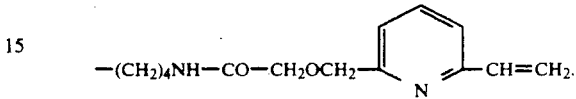

11. A composition comprising (1) a member selected from the group consisting of (i) a coupling compound according to claim 2, (ii) a complex of said coupling compound with a di or tripositive metal atom having a co-ordination number of from 2 to 6, and (ii) a pharmaceutically acceptable salt of said coupling compound, in combination with (2) a pharmaceutically acceptable carrier.

* * * * *